(12) United States Patent
Zhu et al.

(10) Patent No.: US 7,057,398 B2
(45) Date of Patent: Jun. 6, 2006

(54) MICROWAVE SPECTROMETER

(76) Inventors: Zhangwu Zhu, 2444 Forest Dr., Apt. 207, Woodridge, IL (US) 60517; Warren P. Dickinson, 2308 184th St., Lansing, IL (US) 60438

( * ) Notice: Subject to any disclaimer, the term of this patent is extended or adjusted under 35 U.S.C. 154(b) by 0 days.

(21) Appl. No.: 10/361,508

(22) Filed: Feb. 11, 2003

(65) Prior Publication Data

US 2004/0155664 A1  Aug. 12, 2004

(51) Int. Cl.
  *G01R 27/04*  (2006.01)
  *G01R 27/32*  (2006.01)
(52) U.S. Cl. ....................... 324/639; 324/636
(58) Field of Classification Search .............. 324/639, 324/637, 629, 600, 313, 314, 316, 464, 636, 324/640, 647, 76.14, 76.19, 76.22; 422/1–4, 422/26, 28, 34, 62, 105, 112, 113, 117, 119, 422/83, 82.09, 292, 295, 298, 305; 73/23.2, 73/23.4, 23.41, 23.42, 24.04, 24.06, 25.04, 73/25.05, 29.01, 29.05, 30.04, 31.05
See application file for complete search history.

(56) References Cited

U.S. PATENT DOCUMENTS

| | | | | |
|---|---|---|---|---|
| 3,866,118 | A | * | 2/1975 | Ghosh et al. ............... 324/639 |
| 4,873,481 | A | * | 10/1989 | Nelson et al. ............... 324/640 |
| 5,057,782 | A | * | 10/1991 | Brown et al. ............... 324/639 |
| 5,212,099 | A | * | 5/1993 | Marcus ........................ 436/172 |
| 5,399,314 | A | * | 3/1995 | Samuel et al. ................ 422/34 |
| 5,507,173 | A | * | 4/1996 | Shearer et al. ............... 73/23.2 |
| 5,521,360 | A | * | 5/1996 | Johnson et al. ............. 219/709 |
| 5,548,217 | A | * | 8/1996 | Gibson et al. ............... 324/316 |
| 5,679,477 | A | * | 10/1997 | Nishimura et al. ........... 429/49 |
| 6,108,096 | A | * | 8/2000 | Ushio et al. ................. 356/432 |
| 6,387,332 | B1 | * | 5/2002 | Dickinson et al. .......... 422/117 |
| 6,526,805 | B1 | * | 3/2003 | Babes-Dornea et al. ... 73/19.12 |
| 6,527,398 | B1 | * | 3/2003 | Fetzer ......................... 356/437 |
| 2001/0027678 | A1 | * | 10/2001 | Mottram et al. ............. 73/23.2 |
| 2002/0144681 | A1 | * | 10/2002 | Cewers et al. ......... 128/203.17 |
| 2003/0021724 | A1 | * | 1/2003 | McVey ........................ 422/28 |

OTHER PUBLICATIONS

Z. Zhu et al., "A microwave spectrometer with a frequency control system employing a frequency "scanning window" locked to the rotational absorption peak," *Rev. Sci. Instrum.* vol. 66, No. 10, pp. 4817-4823, Oct. 1995.

Z. Zhu et al., "Specificity, accuracy, and interpretation of measurements of ethylene oxide gas concentrations during sterilization using a microwave spectrometer", *Rev. Sci. Instrum.* vol. 68, No. 7, pp. 2883-2890, Jul. 1997.

* cited by examiner

Primary Examiner—Vincent Q. Nguyen
Assistant Examiner—Hoai-An D. Nguyen
(74) Attorney, Agent, or Firm—Levenfeld Pearlsteir

(57) ABSTRACT

An improved microwave spectrometer for measuring the concentration of ethylene oxide gas and the concentration of water vapor in one or more gas samples taken from an ethylene oxide sterilization chamber.

17 Claims, 3 Drawing Sheets

MICROWAVE SPECTROMETER

1. FIELD OF THE INVENTION

This invention relates to an improved microwave spectrometer and, more particularly, to an improved microwave spectrometer which measures the concentrations of specified gases in a one or more gas samples or sample atmospheres.

2. BACKGROUND OF THE INVENTION

Microwave spectrometers have been used to measure the concentration of a specified gas in gas samples or sample atmospheres. For instance, microwave spectrometers have been employed in ethylene oxide sterilization systems to measure the concentration of ethylene oxide gas in gas samples obtained from ethylene oxide sterilization chambers. One such microwave spectrometer is disclosed in the publication entitled *Specificity, Accuracy, And Interpretation Of Measurements Of Ethylene Oxide Gas Concentrations During Sterilization Using A Microwave Spectrometer* published in the Rev. Sci. Instrum. (68) 7, Jul. 1997, which is incorporated herein by reference. The measurement obtained from the microwave spectrometer can be used to determine if a sufficient quantity or concentration of ethylene oxide gas which is necessary to sterilize the articles in the sterilization chamber is present in the sterilization chamber. If a sufficient concentration of ethylene oxide gas is present in the sterilization chamber for a predetermined minimum period of time and certain other conditions are satisfied, the articles being sterilized may be released to the marketplace as properly sterilized. This release of the articles based on the level of ethylene oxide in the sterilization chamber and other conditions without reliance on biological indicators is generally referred to as parametric release.

The relative humidity of the atmosphere in a sterilization chamber during the sterilization process is one of the conditions which may affect the effectiveness of the ethylene oxide sterilization process. For example, in certain ethylene oxide sterilization chambers, if the relative humidity in the sterilization chamber is above a certain percentage (i.e., approximately thirty-three percent) or below a certain percentage (i.e., approximately ninety percent), the interaction between the ethylene oxide gas and the articles being sterilized in the chamber may vary and may affect the sterilization process. Accordingly, to accomplish parametric release for the ethylene oxide sterilization process, it is necessary to know the relative humidity of the atmosphere inside the sterilization chamber during the sterilization process.

Various apparatus are known to measure the relative humidity in a gas sample or sample atmosphere. Furthermore, microwave spectrometers have been tested for measuring concentration of both ethylene oxide and water vapor. One such microwave spectrometer is disclosed in the publication entitled *A Microwave Spectrometer With A Frequency Control System Employing A Frequency "Scanning Window" Locked To The Rotational Absorption Peak* published in the Rev. Sci. Instrum. 66 (10), October 1995, which is incorporated herein by reference. This system employed a single microwave detector and used a dew point generator for calibration of the instrument for measuring water vapor. However, the dew point generator did not function adequately. A need therefore remains for an accurately calibrated microwave spectrometer which accurately and reliably measures the concentration of ethylene oxide and the concentration of water vapor in one or more gas samples taken from an ethylene oxide sterilization chamber and determines the relative humidity in the gas samples.

3. SUMMARY OF THE INVENTION

The present invention solves the above problem by providing an improved microwave spectrometer which alternately measures the concentration of a specified gas and the concentration of water vapor in one or more gas samples, and in particular, the concentration of ethylene oxide gas and the concentration of water vapor in one or more gas samples taken from an ethylene oxide sterilization chamber. The improved microwave spectrometer measures percent by volume of the water vapor and calculates the relative humidity based on thermodynamic data. The improved microwave spectrometer thereby facilitates parametric release of articles undergoing sterilization in an ethylene oxide sterilization facility by measuring the concentration of the water vapor and determining the relative humidity inside the sterilization chamber which affects the overall effectiveness of the ethylene oxide sterilization process.

The microwave spectrometer of the present invention is controlled by printed circuit boards and a computer control system (collectively the control system) and includes two microwave generators which respectively generate microwaves approximately at the absorption frequencies of the ethylene oxide gas and water vapor molecules. Depending on whether the microwave spectrometer is measuring the ethylene oxide gas or the water vapor in the gas samples obtained from the sterilization chamber, the computer control system cause the appropriate microwave generator to generate microwaves. The microwaves are directed to a tuning cavity which precisely refines the frequency of the microwaves to the absorption frequencies of the ethylene oxide molecule or the water vapor molecules as appropriate. After the microwaves are precisely tuned by the tuning cavity, they are directed to an attenuator which adjusts the amplitude or power of the microwaves. The attenuator directs the microwaves to a gas measurement cell where the microwaves interact with any gas molecules in the gas measurement cell having an absorption frequency equal to the frequency of the microwaves as they travel through the gas measurement cell. The microwaves are directed to one of two microwave detectors which detect the amplitude of the microwaves having a frequency equal to the ethylene oxide absorption frequency or the water vapor absorption frequency. The detectors send the measurements they make to the control system which determines the concentration of the ethylene oxide gas or concentration of water vapor molecules in the gas samples based on the amount of power absorbed by the molecules in the gas measurement cell which is the difference between the power of the microwaves regulated by the attenuator and the power of the microwaves determined by detectors. The control system uses these measurements to determine the relative humidity inside the sterilization chamber.

The microwave spectrometer includes a joint calibration/sampling and dilution gas system having a gas manifold which collects the gas samples before they are communicated or sent to the gas measurement cell. The joint calibration/sampling and dilution gas system obtains three types of gas sample. The first gas sample is taken from an ethylene oxide lecture bottle or other suitable source and has a known concentration of ethylene oxide gas. The microwave spectrometer calibrates itself using this gas sample by measuring the concentration of ethylene oxide gas in this gas sample and comparing the measurement to the actual known concentration. The second gas sample is taken from a beaker containing a known concentration of water vapor. The microwave spectrometer calibrates itself using this sample atmosphere by measuring the concentration of water vapor in this sample and comparing the measurement to the actual known concentration. The third gas sample is taken from a sterilization chamber and has an unknown concentration of ethylene oxide gas and an unknown concentration of water vapor. After the calibration procedures, which generate a calibration curve, the microwave spectrometer measures the concentration of ethylene oxide gas molecules and water vapor molecules in this gas sample or in several such gas samples obtained from the sterilization chamber. Using the calibration curves, the microwave spectrometer thereby measures the concentration of ethylene oxide and water vapor in the gas samples. The concentration of water vapor is the absolute humidity inside the sterilization chamber. The control system then determines the relative humidity in the gas samples and thus the sterilization chamber based on the absolute humidity.

It is therefore an object of the present invention to provide an improved microwave spectrometer which alternately measures the concentration of a specified gas and the concentration of water vapor in one or more gas samples or sample atmospheres.

A further object of the present invention is to provide an improved microwave spectrometer which alternately measures the concentration of ethylene oxide gas and concentration of water vapor in one or more gas samples taken from an ethylene oxide sterilization chamber and determines the relative humidity in such gas samples.

Yet another object of the present invention is to provide an improved microwave spectrometer which calibrates itself to measure the concentration of ethylene oxide gas in one or more gas samples, calibrates itself to measure the concentration of water vapor in one or more gas samples, and measures the concentration of ethylene oxide gas and water vapor in one or more gas samples.

Other objects, features and advantages of the present invention will be apparent to those of ordinary skill in the art from the following detailed disclosure in conjunction with the accompanying sheets of drawings, wherein like reference numerals refer to like parts.

4. DESCRIPTION OF THE DRAWINGS

5. DETAILED DESCRIPTION OF THE PREFERRED EMBODIMENT

Figure 1:
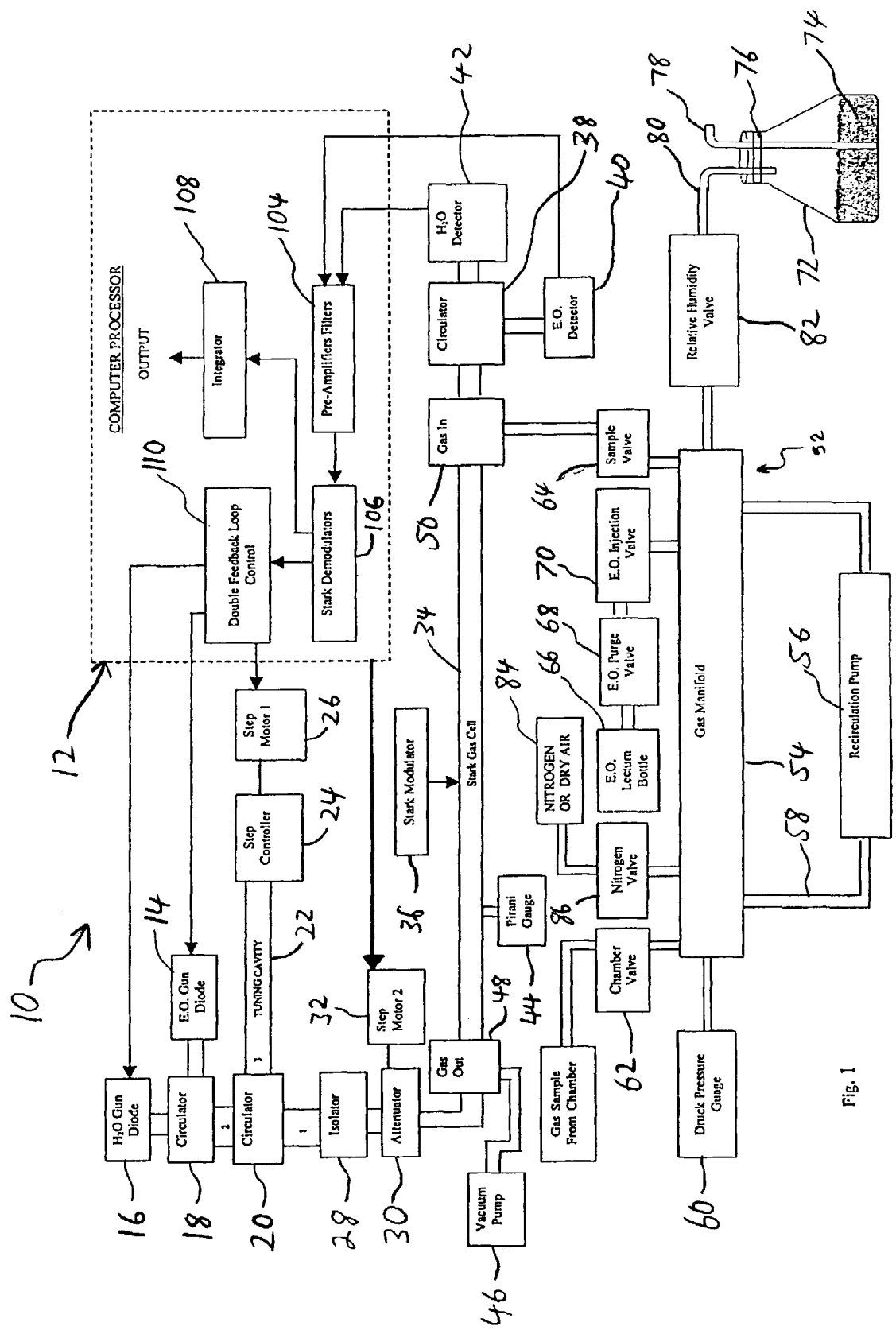
FIG. 1 is a schematic diagram of a microwave spectrometer made in accordance with the present invention.

The improved microwave spectrometer of the present invention, generally indicated by numeral 10, is schematically illustrated in FIG. 1. The improved microwave spectrometer of the present invention is described herein in reference to a microwave spectrometer for alternately measuring the concentration of ethylene oxide gas and the concentration of water vapor in one or more samples or sample atmospheres taken from an ethylene oxide sterilization chamber. However, it should be appreciated that the improved microwave spectrometer of the present invention could be used to measure the concentration of one or more specified gases in one or more gas samples or sample atmospheres taken from another source.

According to principles of quantum physics, a gas molecule will absorb the energy or power of microwaves having a specific frequency. Different gas molecules will absorb the energy or power of microwaves at different specific frequencies. The frequency at which a gas molecule will absorb microwave radiation is called the "absorption frequency". The exact absorption frequencies for a large number of gas molecules have been determined and were published in 1968 by the United States Bureau of Standards. The absorption frequency for an ethylene oxide gas molecule employed in the ethylene oxide sterilization process is 23.134 gigahertz. The absorption frequency for a water vapor molecule is 22.235 gigahertz. To measure the concentration of both the ethylene oxide molecules and water vapor molecules in gas samples or sample atmospheres taken from an ethylene oxide sterilization chamber, the improved microwave spectrometer of the present invention alternately generates microwaves at the absorption frequencies of both molecules, as described below.

The microwave spectrometer 10 is generally constructed or assembled from commercially available components. The microwave spectrometer is controlled by conventional computer and printed circuit board control system 12 which will jointly be referred to herein as a control system 12. The control system 12 includes a plurality of printed circuit boards and computer processor which performs the various functions described below. The microwave spectrometer 10 includes two microwave generators or gun diode oscillators 14 and 16, respectively, which generate microwaves at the absorption frequencies of the ethylene oxide gas and water vapor molecules. In particular, gun diode 14 generates microwaves having a small distribution of frequencies about the absorption frequency for the ethylene oxide molecule and gun diode 16 generates microwaves having a small distribution of frequencies about the absorption frequency for the water vapor molecule. Each gun diode may include a built-in varactor which electronically tunes the frequency of the microwave spectrometer.

The control system 12 directs the appropriate gun diode to generate microwaves depending on whether the microwave spectrometer 10 is measuring the ethylene oxide gas or the water vapor in the gas samples. Both gun diodes 14 and 16 are connected to a first circulator 18. The circulator 18 prevents the microwaves generated from the gun diodes 14 and 16 from re-entering the gun diodes and ensures that the microwaves are channeled in the appropriate direction from the gun diodes 14 and 16 to a second circulator 20. The circulator 20 directs the microwaves into and out of the tuning cavity 22 and specifically into, and/or out of, port 1, port 2 and port 3. The circulators 18 and 20 thereby co-act to properly collect and direct the microwaves generated by the gun diodes 14 and 16 to a tuning cavity 22.

The tuning cavity 22 refines or modulates the microwave frequencies generated by the gun diodes 14 and 16 to the exact absorption frequencies of the ethylene oxide molecule or the water vapor molecule as appropriate. The tuning cavity 22, preferably consists of an empty metal (preferably brass) rectangular section of tube although it could be made of other suitable materials, shapes and sizes. By changing the length of the tube, the microwaves are precisely tuned by their travel in the tube to the absorption frequency of either the specific ethylene oxide molecule or water vapor molecule as appropriate. Specifically, the frequencies of the microwaves are precisely tuned by the distance the microwaves travel in the tube, and by the distance the microwaves that are reflected off the far end wall of the tube travel back in the tube to the circulator 20. The length of the tuning cavity 22 is changed to the exact length necessary to create the appropriate resonant frequency by altering the position (by fractions of millimeters) of the far end wall of the tube which is opposite the circulator 20. The position of the far end wall is altered by a step controller 24 attached to the tube which is driven by an electric step motor 26. Based on commands from the computer control system 12, the step motor 26 drives the step controller 24 to adjust the position of the far end wall and thereby the length of the tube. Accordingly, the tuning cavity must have extremely tight tolerances and must strictly comply with desired manufacturing specifications.

After the microwaves are precisely tuned by the tuning cavity 22, they are channeled back through the second circulator 20 to an isolator 28. The second circulator 20 channels the precisely tuned microwaves so that they do not re-enter the tuning cavity 22. The isolator 28 prevents the microwaves from being reflected back to the circulator 20 or the tuning cavity 22. The isolator 28 also channels the microwaves to an attenuator 30. The attenuator 30 modulates (i.e., reduces) the amplitude of the microwaves as necessary based on commands from the control system 12 to obtain the desired power or energy level for the microwaves (i.e., so that the microwave signal is constant.) The attenuator 30 is controlled by a second step motor 32 which adjusts the power level. The step motor 32 is controlled by the control system 12. The attenuator directs the microwaves to a gas measurement cell 34, and in particular through a microwave input port in one end of the gas measurement cell 34. The control system 12 thereby determines, regulates and knows the amplitude, power or energy level of the microwaves before the microwaves enter the gas measurement cell 34.

Figure 3:
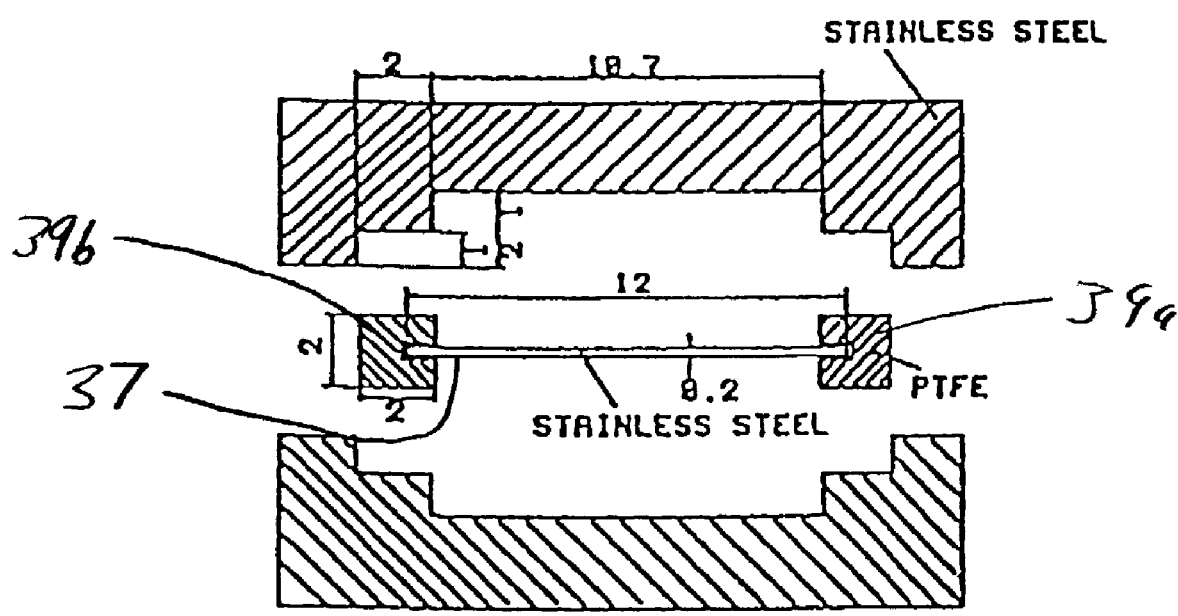
FIG. 3 is an enlarged schematic cross-sectional view of the gas measurement cell (i.e., Stark Gas Cell) in FIG. 1 and a Stark modulator therein.

The gas measurement cell 34 is also referred to as a Stark gas cell because it includes a Stark modulator 36 of the kind well known in the field. The Stark modulator 36, the structure of which is generally illustrated in FIG. 3, includes a standard steel electrode 37 mounted on teflon insulators 39a and 39b. The microwaves, which are modulated by the Stark modulator 36 travel through the gas measurement cell 34 and exit the gas measurement cell 34 through a microwave output port at the opposite end of the gas measurement cell 34. The gas measurement cell 34 is preferably a fifty centimeter rectangular brass tube although it could be made of other suitable materials, shapes and sizes. The modulated microwaves having a specific frequency traveling through the gas measurement cell 34 will interact with any gas molecules in the gas measurement cell 34 having an absorption frequency equal to the specific frequency of the microwaves, as described below.

A third circulator 38 is connected to a microwave output port of the gas measurement cell 34. Two solid state tunable microwave detectors 40 and 42 are connected to the circulator 38. The Ethylene Oxide (E.O.) detector 40 detects the amplitude, power or energy of the microwaves having a frequency approximately equal to the ethylene oxide absorption frequency after the microwaves have traveled through the gas measurement cell 34. The water vapor ($H_2O$) detector 42 detects the amplitude, power or energy level of the microwaves having a frequency approximately equal to the water vapor absorption frequency after the microwaves have traveled through the gas measurement cell 34. The circulator 38, upon commands from the control system 12, directs the microwaves to the appropriate detector depending on whether the microwave spectrometer 10 is measuring the concentration of ethylene oxide gas in the gas sample or the water vapor in the gas sample. The detectors 40 and 42 send the measurements they make to the control system 12. The control system 12 determines the concentration of the ethylene oxide or water vapor molecules by determining the amount of power absorbed by the molecules in the gas measurement cell 34 based on the difference in the power or energy of the microwaves regulated by the attenuator and the power or energy of the microwaves measured by detectors 40 and 42.

A Pirani pressure gauge or transducer 44 measures the pressure in the gas measurement cell 34. The pressure in the gas cell 34 is preferably maintained at a relatively low pressure and particularly at about $\frac{1}{10}$ of a millibar to prevent the ethylene oxide molecules or the water vapor molecules from frequently bumping into each other based on rotational energy levels which may disrupt the microwave absorption process. The Pirani pressure gauge 44 sends a signal to the control system 12 indicating the pressure in the gas measurement cell 34. The control system 12 will vary the pressure in the gas measurement cell 34 by sending signals to a vacuum pump 46 which is connected to a gas output port 48 in the gas measurement cell 34. The vacuum pump 46, based upon commands from the control system 12, increases or decreases the pressure in the gas measurement cell 34 and is also adapted to draw gas samples into the gas measurement cell 34 through a gas input port 50. The gas input port 50 in the gas measurement cell 34 is connected to a joint calibration/sampling and dilution gas system 52. The vacuum pump 46 may continuously draw on or may draw at desired intervals gas sample into the gas measurement cell 34. Single or multiple measurements are made in the gas measurement cell 34. The vacuum pump then exhausts the gas samples from the gas measurement cell 34.

There are three types of gas samples which are measured in the gas measurement cell 34. The first gas sample is taken from the ethylene oxide sterilization chamber which may include both ethylene oxide gas and water vapor. The second is a gas sample which has a known concentration of ethylene oxide gas and is used to calibrate the microwave spectrometer for correctly measuring the concentration of ethylene oxide gas. The third is a gas sample which has a known concentration of water vapor and is used to calibrate the microwave spectrometer for correctly measuring the concentration of water vapor.

The joint calibration/sampling and dilution gas system 52, which is also herein referred to as the gas sampling system 52, includes a gas manifold 54 which collects the gas samples before they are communicated to the gas measurement cell 34. A recirculation pump 56 and recirculation loop 58 are suitably connected to the gas manifold 54 to draw gas samples into and to mix the gas samples in the gas manifold 54. A Druck pressure gauge 60 is also connected to the gas manifold 54 for measuring the pressure in the gas manifold 54. To obtain the first type of gas sample, the gas sampling system 52 includes a chamber valve 62 which is controlled by the control system 12. The chamber value 62 opens to allow a gas sample obtained from the ethylene oxide sterilization chamber into the gas manifold 54. When a gas sample is taken from the sterilization chamber and the chamber valve 62 is opened, the gas sample is drawn into the gas manifold 54 by the recirculation pump 56. The gas sampling system 52 includes a sample valve 64 connected to the gas manifold 54 and the gas input port 54 of the gas measurement cell 34. The control system 12 signals the sample valve 64 to open allowing the gas sample collected in the gas manifold 54 to be drawn into the gas measurement cell 34 to facilitate the microwave spectrometers' measurement of the gas sample. The gas sampling system 52 is thereby suitably connected to the ethylene oxide sterilization chamber and facilitates obtaining one or more gas samples from the sterilization chamber for the microwave spectrometer 12 to measure.

The gas sampling system 52 obtains the second gas sample described above to calibrate the microwave spectrometer for measuring the concentration of ethylene oxide gas. The gas sampling system 52 includes an ethylene oxide lecture bottle 66 containing pure ethylene oxide. The lecture bottle 66 is connected to the gas manifold 54 through an ethylene oxide purge valve 68 and an ethylene oxide injector valve 70. When the computer control system 12 calibrates the microwave spectrometer 10 to measure ethylene oxide gas, the computer control system 12 sends signals to the ethylene oxide purge valve 68, the ethylene oxide injector valve 70 and the nitrogen valve 86 (described below) which coact to inject ethylene oxide vapor and nitrogen into the gas manifold 54. Actual known concentrations of ethylene oxide gas are thereby prepared and input into the gas measurement cell 34 to calibrate the microwave spectrometer for measuring the concentration of ethylene oxide gas.

Figure 2:
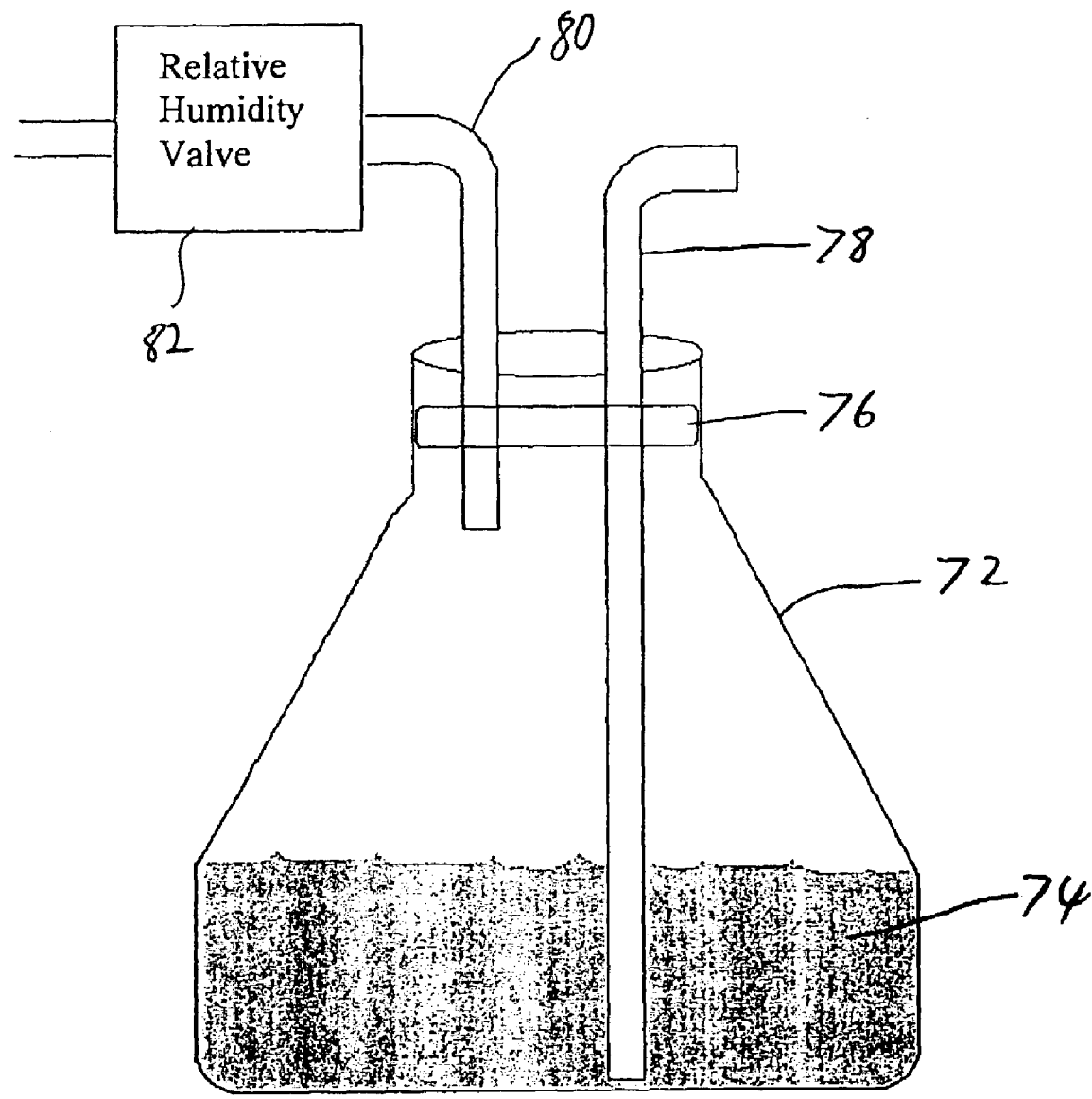
FIG. 2 is an enlarged schematic diagram of the relative humidity valve and relative humidity calibration beaker of the microwave spectrometer of FIG. 1.

The gas sampling system 52 obtains the third gas sample described above to calibrate the microwave spectrometer 10 for measuring the concentration of water vapor. As illustrated in FIGS. 1 and 2, the gas sampling system 52 includes a calibration beaker 72 containing a mixture or solution 74 of water and sodium chloride which produces water vapor having a certain desired percentage relative humidity. A conventional stopper 76 having two passageways therein is mounted in the top of the beaker 72. Two tubes 78 and 80 extend through the passageways in the stopper 76 and into the beaker 72. The first tube 78 extends in the beaker 72 into the solution 74, and outside of the beaker. Air is drawn through tube 78 into the beaker 72 and specifically into the solution 74. The first tube 78 may include a suitable filter or may be attached to a desired specific gas source. The second tube 80 extends in the beaker 72 in the atmosphere above the solution 74, and outside of the beaker 72 is connected to the relative humidity valve 82. The relative humidity valve 82 is connected to the gas manifold 54. A conventional sensor may be disposed in the beaker 72 to measure the standard concentration of the vapor in the beaker.

When the computer control system 12 calibrates the microwave spectrometer to take measurements of the water vapor, the computer control system 12 sends a signal to the relative humidity valve 82 and the nitrogen valve 86 to open which draws a gas from the beaker 72 and nitrogen gas into the gas manifold 54. More specifically, the gas sample containing the water vapor in the beaker 72 above the solution 74 is drawn into the gas manifold 54 through the tube 80 and air or a specified gas is drawn into the beaker 72 and into the solution 74 through tube 78. Actual known concentrations of water vapor are thereby obtained and input into the gas measurement cell 34 to calibrate the microwave spectrometer 10 for measuring the concentration of the water vapor.

The gas sample obtained from the sterilization chamber, the lecture bottle 66 and the beaker 72 are preferably diluted in the gas manifold 54 before they are drawn into the gas measurement cell 34. For this purpose, a suitable source 84 of nitrogen, dry air or other suitable gas is connected to the gas manifold 54 through a nitrogen valve 86. Prior to opening the sample valve 64 and allowing a gas sample to enter the gas measurement cell 34, the control system 12 sends a signal to the nitrogen valve 86 which opens to allow nitrogen gas (or another suitable gas) into the gas manifold 54.

The principal of calibration is in part based on the ideal gas law which provides that in a gas mixture, the sum of the partial pressures of the constituents of that gas mixture equals the total pressure of the system. The concentration of any individual constituent of the mixture can be expressed as the partial pressure divided by the total pressure. Since a certain amount of water vapor is present in the gas samples taken from the ethylene oxide sterilization chamber which is operated approximately at forty to fifty degrees centigrade. The gas sample is preferably diluted with nitrogen gas or another suitable gas by a factor of five, which reduces the number of molecules in the sample atmosphere to obtain better measurements. The dilution provides an ancillary benefit, in terms of calibration, that when there are fewer molecules to be measured, the width of that microwave absorption peak is narrower. More detailed information regarding the gas dilution of the sample atmospheres is well known and described in an article entitled *Quantitative Measurement of Analyte Gases in a Microwave Spectrometer Using Dynamic Sampling Method* published in Rev. Sci. Instrum., Vol. 67, No. 7, July 1996, which is incorporated herein by reference.

The control system 12 of microwave spectrometer 10 is connected to gun diodes 14 and 16, circulators 18 and 20, step motors 26 and 32, circulator 38, detectors 40 and 42, gauges 44 and 60, pumps 46 and 56, and valves 62, 64, 68, 70, 82 and 86 to control, regulate and obtain information necessary for the operation of the microwave spectrometer 10. The control system 12 includes a conventional computer processor, a pre-amplifier filter 104 for filtering the signal obtained from the detectors 40 and 42, one or more stark demodulators 106 for demodulating the signal modulated by the Stark modulator 36, an integrator 108, and a double feedback loop control 110 for sending signals to the gun diodes 14 and 16.

There are five general steps involved in measuring gas samples. First, the gas manifold 54 is cleaned to eliminate all of the gas that has been in the gas manifold 54, recirculation pump 56 and recirculation loop 58 from previous measurements. To clean the gas manifold 54, the recirculation pump 56 is turned on by the computer control system 12 and the gas manifold 54 is flushed with a suitable atmosphere. Second, a gas sample is obtained in the gas manifold 54 from the sterilization chamber or for calibration purposes from the E.O. lecture bottle 66 or the calibration beaker 72. Third, whether for calibration purposes or for an actual measurement, the gas sample is diluted with nitrogen gas or another suitable gas by a suitable factor (preferably five) and mixed by the recirculation pump 56. Fourth, the gas sample is channeled from the gas manifold 54 to the gas measurement cell 34 where the microwaves interact with the gas sample and then to exhaust.

More specifically, the microwave spectrometer preferably will first calibrate itself for measuring both ethylene oxide gas and water vapor. To calibrate itself for ethylene oxide gas measurements, the gas manifold 54 is cleaned and a diluted gas sample having a known concentration of ethylene gas molecules is obtained in the gas manifold 54. The E.O. gun diode 14 generates microwaves which are directed through circulators 18 and 20 to the tuning cavity 22. The microwaves are tuned in the tuning cavity 22 and redirected through the circulator 20 into the isolator 28 and then to the attenuator 30 which modulates the amplitude of the microwaves. The microwaves are directed into the gas measurement cell 34 where they are subjected to Stark modulation.

The gas sample in the gas manifold 54 having a known concentration of ethylene oxide gas is channeled from the gas manifold 54 to the gas measurement cell 34 where the microwaves interact with the gas sample. The ethylene oxide molecules absorb the energy of the microwaves having a frequency equal to the absorption frequency of the ethylene oxide molecules. The circulator 38 directs the microwaves to the E.O. detector 40 which measures the amplitude of the microwaves. The detector 40 sends this measurement to the control system which determines how much power was absorbed by the ethylene oxide gas in the gas sample as the microwaves traveled through the gas measurement cell 34. After the measurement is taken, the gas sample is exhausted from the gas measurement cell 34.

If the amount of power detected is less than the amount of power which enters the gas measurement cell 34, the control system 12 determines the absorbed power and the concentration of ethylene oxide gas in the gas sample in the gas measurement cell 34. During the calibration adjustment procedure, since the concentration of the ethylene oxide gas is known, the control system determines if the concentration of ethylene oxide it determined is accurate. If the measurement is accurate, the control system knows that it is accurately measuring the concentration of ethylene oxide in the gas sample and no adjustment is made. If the measurement is inaccurate, the control system makes an offset adjustment to match the calibration curve.

After calibrating for measurement of the ethylene oxide gas molecules, the microwave spectrometer preferably will then calibrate itself for measuring the water vapor. To calibrate itself for water vapor measurements, the gas manifold 54 is cleaned and a diluted gas sample having a known concentration of water vapor is obtained in the gas manifold 54. The $H_2O$ gun diode 16 generates microwaves which are directed through circulators 18 and 20 to the tuning cavity 22. The microwaves are tuned in the tuning cavity and redirected through the circulator 20 into the isolator 28 and then to the attenuator 30 which modulates the amplitude of the microwaves. The microwaves are directed into the gas measurement cell 34 where they are subject to Stark modulation.

The gas sample in the gas manifold having a know concentration of water vapor is channeled from the gas manifold 54 to the gas measurement cell 34 where the microwaves interact with the gas sample. The water vapor molecules absorb the energy of the microwaves having a frequency equal to the absorption frequency of water vapor molecules. The circulator 38 directs the microwaves to the $H_2O$ detector 42 which measures the amplitude of the microwaves. The detector 42 sends this measurement to the control system 12 which determines how much power was absorbed by the water vapor in the gas sample as the microwaves traveled through the gas measurement cell 34. After the measurement is taken, the gas sample is exhausted from the gas measurement cell 34.

If the amount of power detected is less than the amount of power which enters the gas measurement cell 34, the control system 12 determines the absorbed power and the concentration of water vapor in the gas sample in the gas measurement cell 34. During the calibration procedure, since the concentration of the water vapor molecules is known, the computer control system determines if the concentration of water vapor it determined is accurate. If the measurement is accurate, the computer control system knows that it is accurately measuring the concentration of water vapor in the sample atmosphere and makes no adjustment. If the measurement is inaccurate, the control system makes an offset adjustment to match the calibration curve.

After the appropriate calibration procedures, the microwave spectrometer is ready to take measurements of the gas samples obtained from the sterilization chamber. The gas manifold 54 is cleaned and a diluted gas sample is obtained from the sterilization chamber. The microwave spectrometer may first measure the concentration of the ethylene oxide gas in the gas sample. Similar to the ethylene oxide calibration procedure, the E.O. gun diode 14 generates microwaves which are directed through circulators 18 and 20 to the tuning cavity 22. The microwaves are tuned in the tuning cavity and redirected through the circulator 20 into the isolator 28 and then to the attenuator 30 which modulates the amplitude of the microwaves. The microwaves are directed into the gas measurement cell 34 where they are subject to Stark modulation. The gas sample in the gas manifold 54 having an unknown concentration of ethylene oxide gas is channeled from the gas manifold 54 to the gas measurement cell 34 where the microwaves interact with the gas sample. The ethylene oxide gas in the gas sample absorbs the energy of the microwaves having a frequency equal to the absorption frequency of the ethylene oxide molecules. The circulator 38 directs the microwaves to the E.O. detector 40 which measures the amplitude of the microwaves. The detector 40 sends this measurement to the control system which determines how much power was absorbed by the ethylene oxide gas in the gas sample as the microwaves traveled through the gas measurement cell 34. The microwave spectrometer thereby determines the concentration of the ethylene oxide gas in the gas sample taken from the sterilization chamber. Multiple measurements may be taken of the concentration of the ethylene oxide gas in the gas sample and several gas samples may be measured.

After the measurements are taken, the gas sample may be exhausted from the gas manifold 54 and a new gas sample can be obtained from the sterilization chamber to measure the relative humidity in the sterilization chamber. Alternatively, the same gas sample which was measured for concentration of ethylene oxide gas may be maintained in the gas measurement cell and the microwave spectrometer may take a measurement of the concentration of water vapor in the same gas sample.

To measure the concentration of water vapor molecules in the gas sample, similar to the water vapor calibration procedure, the $H_2O$ gun diode 16 generates microwaves which are directed through circulators 18 and 20 to the tuning cavity 22. The microwaves are tuned in the tuning cavity and redirected through the circulator 20 into the isolator 28 and then to the attenuator 30 which modulates the amplitude of the microwaves. The microwaves are directed into the gas measurement cell 34 where they are subject to Stark modulation. The microwaves interact with the gas sample in the gas manifold having an unknown concentration of water vapor. The water vapor molecules in the gas sample absorb the energy of the microwaves having a frequency equal to the absorption frequency of water vapor molecules. The circulator 38 directs the microwaves to the $H_2O$ detector 42 which measures the amplitude of the microwaves. The detector 42 sends this measurement to the control system which determines how much power was absorbed by the gas molecules in the gas sample as the microwaves traveled through the gas measurement cell 34. The microwave spectrometer thereby determines the concentration of the water vapor in the gas sample taken from the sterilization chamber.

Multiple measurements may be taken of the concentration of the water vapor in the gas sample and several samples may be measured.

It should be appreciated that the microwave spectrometer could first calibrate itself for measuring water vapor and then calibrate itself for measuring ethylene oxide gas. It should also be appreciated that the microwave spectrometer could calibrate itself for measuring ethylene oxide gas directly prior to measuring the ethylene oxide gas and could calibrate itself for measuring water vapor directly prior to measuring the water vapor.

The improved microwave spectrometer utilizes one or more conventional uninterruptable power supplies which provides uninterrupted power to the computer control system and the entire microwave spectrometer.

All publications, patents and patent applications mentioned in this specification are herein incorporated by reference to the same extent as if each individual publication, patent or patent application was specifically and individually indicated to be incorporated by reference. No admission is made that any reference cited in this specification is prior art.

It will be understood that many modifications and variations may be effected without departing from the spirit of the present invention. Accordingly, this application is limited only by the scope of the appended claims.

What is claimed is:

1. A microwave spectrometer which measures the concentration of an ethylene oxide gas and the concentration of water vapor in one or more gas samples taken from a sterilization chamber, said microwave spectrometer, in combination, comprising:
   a first microwave generator which generates microwaves at the absorption frequency of an ethylene oxide gas molecule;
   a second microwave generator, which generates microwaves at the absorption frequency of a water vapor molecule;
   a tuning cavity, which modulates microwave frequencies generated by said first and second microwave generators to exact absorption frequencies of an ethylene oxide gas molecule and a water vapor molecule;
   a first detector that measures microwaves at the absorption frequency of an ethylene oxide gas molecule;
   a second detector that measures microwaves at the absorption frequency of a water vapor molecule; and
   wherein the microwave spectrometer measures the concentration of an ethylene oxide gas and the concentration of water vapor in one or more gas samples by alternatively generating and detecting microwaves having absorption frequencies of an ethylene oxide gas and water vapor.

2. The microwave spectrometer of claim 1, further comprising a control system connected to the first microwave generator, the second microwave generator, the first detector and the second detector.

3. The microwave spectrometer of claim 1, wherein said tuning cavity and the second microwave generator generates microwaves at the exact absorption frequencies of a water molecule of 22.235 gigahertz.

4. The microwave spectrometer of claim 1, wherein said tuning cavity and the first microwave generator generates microwaves at the exact absorption frequencies of an ethylene oxide gas molecule of 23.134 gigahertz.

5. A method of measuring the concentration of an ethylene oxide gas and the concentration of water vapor in one or more gas samples taken from a sterilization chamber in a microwave spectrometer comprising the following steps, in combination,
   subjecting the gas sample(s) to a first set of microwaves generated at the absorption frequency of an ethylene oxide gas molecule;
   subjecting the gas sample(s) to a second set of microwaves generated at the absorption frequency of a water vapor molecule;
   detecting microwaves at the absorption frequency of an ethylene oxide gas molecule that pass through the gas sample(s); and
   detecting microwaves at the absorption frequency of a water vapor molecule that pass through the gas sample(s); and
   calculating the concentration of an ethylene oxide gas and the concentration of water vapor from the difference in the generated and detected microwaves.

6. The method of claim 5, wherein the second set of microwaves generated are microwaves at the exact absorption frequencies of a water molecule of 22.235 gigahertz.

7. The method of claim 5, wherein the first set of microwaves generated are microwaves at the exact absorption frequency of an ethylene oxide gas molecule of 23.134 gigahertz.

8. A microwave spectrometer which measures the concentration of an ethylene oxide gas and the concentration of water vapor in one or more gas samples taken from a sterilization chamber, said microwave spectrometer, in combination, comprising:
   a first microwave generator which generates microwaves at the absorption frequency of an ethylene oxide gas molecule;
   a second microwave generator which generates microwaves at the absorption frequency of a water vapor molecule;
   a first circulator connected to the first microwave generator and to the second microwave generator;
   a tuning cavity connected to the first circulator and to a second circulator;
   a gas measurement cell connected the first circulator;
   the second circulator connected to the gas measurement cell;
   a first detector connected to the second circulator for measuring microwaves at the absorption frequency of an ethylene oxide gas molecule;
   a second detector connected to the second circulator for measuring microwaves at the absorption frequency of a water vapor molecule; and
   a control system connected to the first microwave generator, the second microwave generator, the tuning cavity, the second circulator, the first detector and the second detector,
   wherein the microwave spectrometer measures the concentration of an ethylene oxide gas and the concentration of water vapor in one or more gas samples by alternatively generating, and tuning and detecting microwaves having absorption frequencies of an ethylene oxide gas molecule and a water vapor molecule.

9. The microwave spectrometer of claim 8, which further includes an isolator connected to the third circulator and the gas measurement cell.

10. The microwave spectrometer of claim 9, which further includes an attenuator connected to the isolator and the gas measurement cell.

11. The microwave spectrometer of claim 8, which further includes a gas sampling apparatus which provides sample atmospheres having a known concentration of an ethylene oxide gas.

12. The microwave spectrometer of claim 8, which further includes a gas sampling apparatus which provides sample atmospheres having a known concentration of water vapor.

13. The microwave spectrometer of claim 12, wherein the gas sampling apparatus includes a water vapor calibration beaker and a relative humidity valve to calibrate said microwave spectrometer for measuring the exact concentration of water vapor.

14. The microwave spectrometer of claim 13, wherein the calibration beaker includes a solution of water for producing water vapor having a known concentration, said water vapor having a certain desired percentage of relative humidity.

15. The microwave spectrometer of claim 14, wherein the solution includes water and sodium chloride.

16. The microwave spectrometer of claim 8, which further includes a third circulator connected to the first circulator and the gas measurement cell.

17. The microwave spectrometer of claim 8, which further includes a gas sampling apparatus which provides a gas sample of an ethylene oxide gas from a sterilization chamber to the gas measurement cell.

* * * * *